United States Patent [19]

Griss et al.

[11] 4,042,711
[45] Aug. 16, 1977

[54] DERIVATIVES OF BIPHENYLOXY-LOWER ALKANOIC ACIDS, SALTS THEREOF AND THEIR USE AS ANTIHYPERLIPIDEMICS

[75] Inventors: Gerhart Griss, Biberach an der Riss; Wolfgang Grell, Biberach an der Riss; Rudolf Hurnaus, Biberach an der Riss; Robert Sauter, Laupheim; Bernhard Eisele, Biberach an der Riss; Nikolaus Kaubisch, Biberach an der Riss; Matyas Leitold, Biberach an der Riss, all of Germany

[73] Assignee: Boehringer Ingelheim GmbH, Ingelheim am Rhein, Germany

[21] Appl. No.: 740,829

[22] Filed: Nov. 11, 1976

Related U.S. Application Data

[63] Continuation-in-part of Ser. No. 643,700, Dec. 23, 1975, Pat. No. 4,010,279.

[30] Foreign Application Priority Data

Jan. 9, 1975 Germany .............................. 2500692
Oct. 25, 1975 Germany .............................. 2547872

[51] Int. Cl.² .............. C07C 103/46; C07C 103/737; C07C 103/84
[52] U.S. Cl. ..................... 424/319; 260/519
[58] Field of Search ......................... 260/519; 424/319

[56] References Cited

U.S. PATENT DOCUMENTS 3,652,646  3/1972  Leigh et al. ............... 260/519 X
3,781,328  12/1973  Witte et al. ............... 260/519 X
3,914,286  10/1975  Mieville ................... 260/471 X Primary Examiner—Richard L. Raymond
Attorney, Agent, or Firm—Hammond & Littell

[57] ABSTRACT

Compounds of the formula

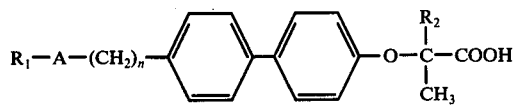

wherein
$R_1$ is straight or branched alkyl of 1 to 6 carbon atoms, cycloalkyl of 3 to 6 carbon atoms, phenylalkyl, phenylalkenyl, pyridyl or

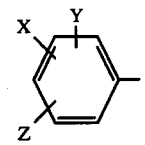

where
X, Y and Z are each hydrogen, halogen, alkyl of 1 to 3 carbon atoms or alkoxy of 1 to 3 carbon atoms,
$R_2$ is hydrogen or alkyl of 1 to 4 carbon atoms,
A is —CO—NH— or —NH—CO—, and
$n$ is 1, 2 or 3, and non-toxic salts thereof formed with an inorganic or organic base; the compounds as well as the salts are useful as antihyperlipidemics.

7 Claims, No Drawings

DERIVATIVES OF BIPHENYLOXY-LOWER ALKANOIC ACIDS, SALTS THEREOF AND THEIR USE AS ANTIHYPERLIPIDEMICS

This is a continuation-in-part of copending application Ser. No. 643,700 filed Dec. 23, 1975, now U.S. Pat. No. 4,010,279. This invention relates to novel biphenyloxy derivatives, as well as to methods of preparing these compounds.

PRIOR ART

It is known that various alkyl phenoxy-propionates have antihyperlipidemic properties.

For instance, British patent 860,303 discloses that ethyl 2-(p-chloro-phenoxy)-2-methyl-propionate has antihypercholesteremic properties.

German Offenlegungsschrift No. 2,149,070 discloses that ethyl 2-methyl-2-{4-[β-(2-methoxy-5-chlorobenzamido)-ethyl]-phenoxy}-propionate exhibits similar properties.

And British patent 1,121,722 discloses that methyl 2-[4-(p-chloro-phenyl)-phenoxy]-2-methyl-propionate has antihyperlipidemic properties.

THE INVENTION

More particularly, the present invention relates to a novel class of biphenyloxy derivatives represented by the formula

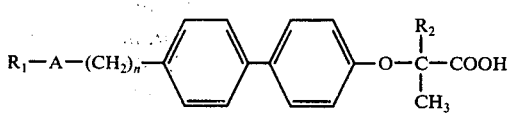

(I)

wherein $R_1$ is straight or branched alkyl of 1 to 6 carbon atoms, cycloalkyl of 3 to 6 carbon atoms, phenylalkyl, phenylalkenyl, pyridyl or

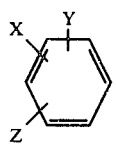

where

X, Y and Z are each hydrogen, halogen, alkyl of 1 to 3 carbon atoms or alkoxy of 1 to 3 carbon atoms,
$R_2$ is hydrogen or alkyl of 1 to 4 carbon atoms,
A is —CO—NH— or —NH—CO—, and
$n$ is 1, 2 or 3, and non-toxic salts thereof formed with an inorganic or organic base.

Particularly preferred embodiments of the variants for substituents $R_1$ and $R_2$ are the following:

$R_1$ — Methyl, propyl, pentyl, hexyl, phenyl, benzyl, phenethyl, tolyl, fluorophenyl, chlorophenyl, bromophenyl, 2-methoxy-5-chloro-phenyl, dimethoxyphenyl, trimethoxy-phenyl or phenylethenyl; and
$R_2$ — Hydrogen or methyl.

The compounds embraced by formula I may be prepared by the following methods:

Method A

By reacting a hydroxy-biphenylyl derivative of the formula

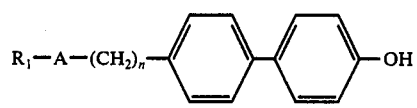

(II)

wherein $R_1$, A and $n$ have the same meanings as in formula I with a compound of the formula

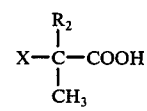

(III)

wherein $R_2$ has the same meanings as in formula I and X is halogen.

The reaction is advantageously carried out in the presence of a solvent, such as methyl ethyl ketone, dimethylformamide of glycol dimethyl ether, and preferably in the presence of a base, such as potassium carbonate or sodium hydride, at temperatures between 0° and 200° C, but preferably at the boiling point of the particular solvent which is used. The reaction may also be carried in the absence of a solvent, the reactants being in the molten state.

Method B

By reacting a diazonium salt of the formula

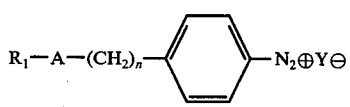

(IV)

wherein
$R_1$, A and $n$ have the same meanings as in formula I and
Y is the anion of an inorganic acid, such as the chloride anion, with a phenoxy derivative of the formula

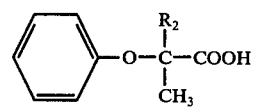

(V)

wherein $R_2$ has the same meanings as in formula I.

The reaction is preferably carried out with a diazonium salt which is formed in situ from a corresponding aniline and sodium nitrite in the presence of an acid, such as hydrochloric acid, and in the presence of a solvent, such as water, water/methanol or water/dioxane, advantageously at temperatures between 0° and 50° C, but preferably at room temperature.

Method C

By hydrolizing a carboxylic acid ester of the formula (XI)

-continued

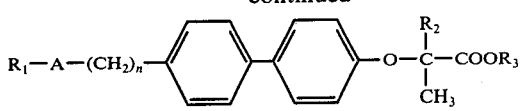

wherein
$R_1$, $R_2$, A and n have the same meanings as in formula I, and
$R_3$ is alkyl of 1 to 6 carbon atoms or cycloalkyl of 3 to 7 carbon atoms.

These compounds of the formula I may be converted into their salts with inorganic or organic bases. Examples of non-toxic, pharmacologically acceptable salts are those formed with sodium hydroxide, potassium hydroxide or cyclohexylamine.

The starting compounds of the formula II are also new and may be prepared by reacting a compound of the formula (VI)

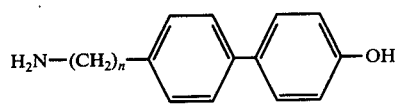

wherein n has the meanings previously defined, with a compound of the formula

 (VII)

wherein
$R_1$ has the same meanings as in formula I and
Z is hydroxyl or halogen;
or by reacting a compound of the formula (VIII)

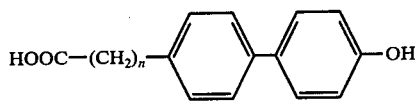

wherein n has the meanings previously defined, or a halide or anhydride thereof, with amine of the formula $R_1NH_2$ where $R_1$ has the same meanings as in formula I.

The reaction is advantageously carried out in the presence of a solvent, such as dioxane or water/dioxane, optionally in the presence of a base, such as potassium carbonate, sodium hydroxide, triethylamine or pyridine, and optionally in the presence of an acid-activating agent, such as cyclohexylcarbodiimide or thionyl chloride, at temperatures between 0° and 100° C.

The starting compounds of the formula VI may be prepared by the following methods:

a. Ether cleavage and hydrolysis of a compound of the formula (IX)

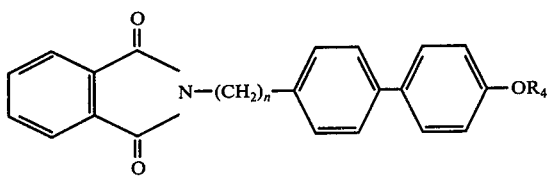

wherein n has the meanings previously defined, and
$R_4$ is lower alkyl of 1 to 3 carbon atoms.

The reaction is preferably carried out in a medium suitable for ether cleavage and hydrolysis, such as hydrobromic acid or hydrobromic acid/glacial acetic acid at elevated temperatures, for example at the boiling point of the particular medium which is used.

b. Reduction of a compound of the formula (X)

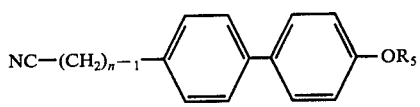

wherein
n has the meanings previously defined, and
$R_5$ is hydrogen or lower alkyl of 1 to 3 carbon atoms, and optional subsequent ether cleavage.

The reduction is preferably carried out in the presence of a solvent, such as methanol or methanol/ammonia, with nascent or catalytically activated hydrogen, for instance with hydrogen in the presence of Raney nickel at a pressure of 50 atmospheres and room temperature. The optional subsequent ether cleavage is advantageously carried out with hydrobromic acid/glacial acetic acid at the boiling point.

The starting compounds of the formula III are either disclosed in the literature, or may be prepared by conventional methods from the corresponding unhalogenated compounds by halogenation.

The starting compounds of the formula IV may be obtained from a corresponding aniline by diazotization with sodium nitrite, and the starting compounds of the formula V by reaction of phenol with a compound of the formula III in the presence of a base.

The preparation of esters of the formula XI is described in the parent application Ser. No. 643,700.

The following examples illustrate the present invention and will enable others skilled in the art to understand it more completely. It should be understood, however, that the invention is not limited solely to the particular examples given below.

Preliminary note:
Some of the end products obtained in the following examples are oils which are very difficult to crystallize and, if at all, crystallize very slowly. Therefore, for the purpose of physical characterization, their M + H values were determined in a Finnigan mass spectrometer 3300 by chemical ionization, using isobutane as the reactant gas.

EXAMPLE 1

2-Methyl-2-{4-[2-(2-methoxy-5-chloro-benzamido)-ethyl]biphenyl-4'-oxy}-propionic acid was prepared by hydrolysis of ethyl 2-methyl 2-{4-[-2-(2-methoxy-5-chloro-benzamido)-ethyl]-biphenyl -4'-oxy}-propionate with potassium hydroxide in water/dioxane (1:9) at room temperature. Yield: 75% of theory; m.p. 184° C. M + H = 468; $M_{calc}$ = 467.96.

Calculated: C—66.75%; H—5.60%; N—2.99%
Found: C—66.60%; H—6.00%; N—2,85%

EXAMPLE 2

2-{4-[2-(2-methoxy-5-chloro-benzamido)-ethyl]-biphenyl-4'-oxy}-propionic acid was prepared from its ethyl ester by alkaline hydrolysis with potassium hydroxide in water/dioxane (1:19) at room temperature. Yield: 66% of theory; m.p. 145° C.

Calculated: C—66.25%; H—5.33%; N—3.04%; Found: C—66.10%; H—5.46%; N—3.14%.

EXAMPLE 3

2-Methyl-2-{4-(2-methoxy-5-chloro-benzamido-methyl)-biphenyl-4'oxy}-propionic acid was prepared by alkaline hydrolysis of ethyl 2-methyl-2-{4-[2-methoxy-5-chloro-benzamido-methyl]-biphenyl-4'-oxy}-propionate in 1 N potassium hydroxide and dioxane (1:5) at room temperature. Yield: 72% of theory; m.p. 104° C.

Calculated: C—66.16%; H—5.34%; N—3.09%; Found: C—66.50%; H—5.31%; N—3.13%.

EXAMPLE 4

2-Methyl-2-{4-[2-(2-methoxy-benzamido)-ethyl]-biphenyl-4'-oxy}-propionic acid by method C 4 gm (8.6 millimols) of ethyl 2-methyl-2-{4-[2-(2-methoxy-benzamido)-ethyl]-biphenyl-4'-oxy}-propionate were hydrolized at room temperature over a period of 12 hours with a solution of 1 gm (17.2 millimols) of potassium hydroxide in 5 ml of water and 95 ml of methanol. After distilling off the methanol, 100 ml of water were added, and the mixture was extracted with ether. The pH of the aqueous phase was adjusted to between 1 and 2 with 2 N hydrochloric acid, and the acid mixture was extracted with chloroform. The combined chloroform extracts were dried over sodium sulfate and evaporated to dryness, and the residue was recrystallized from ether. Yield: 3.2 gm (86% of theory); m.p. 133° C.

Calculated: C—72.03%; H—6.27%; N—3.23% Found: C—71.80% H—6.32%; N—3.28%

EXAMPLE 5

2-Methyl-2-{4-[2-(3-methoxy-benzamido)-ethyl]-biphenyl-4'-oxy}-propionic acid was prepared from its ethyl ester by alkaline hydrolysis analogous to Example 4. Yield: 80% of theory; m.p. 117° C.

Calculated: C—72.10%; H—6.28%; N—3.28% Found: C—71.90%; H—6.45%; N—3.37%

EXAMPLE 6

2-Methyl-2-{4-[2-(4-methoxy-benzamido)-ethyl]-biphenyl-4'-oxy}-propionic acid was prepared from its ethyl ester by alkaline hydrolysis analogous to Example 4. Yield: 82% of theory; m.p. 180°-183° C. M + H = 433; $M_{calc}$ = 433.49.

Calculated: C—71.10%; H—6.28%; N—3.28% Found: C—70.90%; H—6.28%; N—3.49%

EXAMPLE 7

2-Methyl-2-{4-[2-benzamido-ethyl]-biphenyl-4'-oxy}-propionic acid was prepared from its ethyl ester (m.p. 100° C) by alkaline hydrolysis analogous to Example 4. Yield: 82% of theory; m.p. 179° C.

Calculated: C—74.40%; H—6.25%; N-3.48%; Found: C—74.40%; H—6.27%; N—3.43%.

EXAMPLE 8

2-Methyl-2-{4-[2-3,4-dimethoxy-benzamido)-ethyl]-biphenyl-4'-oxy}-propionic acid was prepared from its ethyl ester by alkaline hydrolysis analogous to Example 4. Yield: 80% of theory; m.p. 184° C. M + H = 463; $M_{calc}$ = 463.51.

EXAMPLE 9

2-Methyl-2-{4-[2-(2,3-dimethoxy-benzamido)-ethyl]-biphenyl-4'-oxy}-propionic acid was prepared from its ethyl ester by alkaline hydrolysis analogous to Example 39. Yield: 83% of theory; m.p. 184° C. M + H = 463; $M_{calc}$ = 463.51.

EXAMPLE 10

2-Methyl-2-{4-[2-nicotinoyl-amido-ethyl]-biphenyl-4'-oxy}-propionic acid was prepared from its ethyl ester (m.p. 98° C) by alkaline hydrolysis analogous to Example 4. Yield: 37% of theory; m.p. 179° C. M + H = 404; $M_{calc}$ = 404.45.

Calculated: C—71.40%; H—5.97%; N—6.93%; Found: C—71.50%; H—6.07%; N—6.75%.

EXAMPLE 11

2-Methyl-2-{4-[2-(2-methoxy-benzamido-ethyl]-biphenyl-4'-oxy}-propionic acid by method A 0.5 gm (1.4 millimols) of 4-[2-(2-methoxy-benzamido)-ethyl]-4'-hydroxy-biphenyl were heated at 90°-130° C for 90 minutes with 0.25 gm of 2-bromo-2-methyl-propionic acid. The reaction product was isolated by chromatography on silicagel with chloroform/methanol (9:1) as the eluant. M.P. 133° C. M + H = 433; $M_{calc}$ = 433.50.

EXAMPLE 12

2-Methyl-2-{4-[2-(5-chloro-2-methoxy-benzamido)-ethyl]-biphenyl-4'-oxy}-propionic acid was prepared from 4-[2-(5-chloro-2-methoxy-benzamido)-ethyl]-4'-hydroxy-biphenyl and 2-bromo-2-methyl-propionic acid analogous to Example 11. M.p. 145° C. M + H = 468; $M_{calc}$ = 467.96.

The compounds of the present invention, that is, those embraced by formula I above and their non-toxic, pharmacologically acceptable salts, have useful pharmacodynamic properties. More particularly, they lower the cholesterol and triglyceride level in the blood of warm-blooded animals, such as rats, and are therefore useful as antihyperlipidemics.

The above pharmacologicaly activity of the compounds of this invention, as well as their acute toxicities, were ascertained along with those of the three antihyperlipidemic compounds of the prior art by the standard test methods described below. Tables I and II show the results obtained for some representative species where A = 2-methyl-2-{4-[2-(2-methoxy-5-chloro-benzamido)-ethyl]-biphenyl-4'-oxy}-propionic acid, B = 2-methyl-2-{4-[2-(2-methoxy-benzamido)-ethyl]-biphenyl-4'-oxy}-propionic acid, C = ethyl 2-(4-chlorophenoxy)-2-methyl propionate, D = methyl 2-[4-(4-chlorophenyl)-phenoxy]-2-methyl-propionate, and E = ethyl 2-methyl-2-{4-[2-(2-methoxy-5-chloro-benzamido)-ethyl]-phenoxy}-propionate.

1. Lipid level lowering activity

The test compound was administered twice by an esophageal tube at 20 hours' interval to male normolipemic rats having a body weight of 250-300 gm. When the test began, the animals were deprived of food, but water was freely accessible to them. 28 and 44 hours later the serum cholesterol and triglyceride-levels were determined. The measurement of cholesterol and triglycerides was effected simultaneously, using an autoanalyzer; the percentage depression was calculated, compared with a control group treated with placebo.

The cholesterol-lowering activity of the test compound was observed after oral administration of one dose and after oral administration of various doses. From these data the does leading to a 15% ($ED_{15}$) and a 20% ($ED_{20}$) depression of the cholesterol level in the serum was determined by regression analysis:

TABLE I

| Compound | Time after the beginning of the test in hours | Dose (mg/kg) | Cholesterol level lowering activity | |
|---|---|---|---|---|
| | | | $ED_{15}$ mg/kg | $ED_{20}$ mg/kg |
| Invention: | | | | |
| A | 28 | 1 - 20 | — | 15.97 |
| | 44 | 1 - 20 | — | 4.41 |
| B | 28 | 1 - 10 | — | 3.10 |
| | 44 | 0.5 - 10 | — | 0.59 |
| Prior Art: | | | | |
| C | 28 | 25 - 100 | 15 | 22 |
| | 44 | 25 - 100 | 25 | 32 |
| D | 28 | 1 - 10 | 6.9 | 11 |
| | 44 | 1 - 10 | 4.4 | 5.6 |
| E | 28 | 1 - 25 | 3.6 | 5.0 |
| | 44 | 1 - 50 | 3.6 | 5.0 |

2. Acute toxicity

The acute toxicity was determined on groups of 5 or 6 white mice each, after oral administration of the test compound at dosage levels of 2.5 gm/kg, 5 gm/kg and 10 gm/kg (observation time 14 days).

TABLE II

| Compound | Toxicity ($LD_{50}$) |
|---|---|
| Invention: | |
| A | > 10 gm/kg (0 out of 5 animals died) |
| B | > 2.5 gm/kg (1 out of 5 animals died) |
| Prior Art: | |
| C | 1.7 gm/kg* |
| D | 5 gm/kg (3 out of 5 animals died) |
| E | 2.5 gm/kg (3 out of 6 animals died) |

*see Therapie 27, 385 (1972).

For pharmaceutical purposes the compounds according to the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective antihyperlipidemic dosage unit of the compounds according to the present invention is from 0.08 to 1.67 mgm/kg body weight, preferably 0.08 to 0.5 mgm/kg body weight. The daily dose rate is 0.16 to 5.0 mgm/kg, preferably 0.25 to 1.5 mgm/kg.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 13

Suppositories

The suppository composition is compounded from the following ingredients:

| | |
|---|---|
| 2-Methyl-2-{4-[2-(2-methoxy-5-chloro-benzamido)-ethyl]-biphenyl-4-oxy}-propionic acid | 0.030 parts |
| Suppository base (e.g. cocoa butter) | 1.670 parts |
| Total | 1.700 parts |

Preparation

The milled active ingredient is homogeneously stirred into the suppository base which had previously been melted and cooled to 40° C. 1700 mgm portions of the resulting mixture are poured into cooled suppository molds and allowed to harden therein. Each suppository contains 30 mgm of the active ingredient and is a rectal dosage unit composition with effective antihyperlipidemic action.

EXAMPLE 14

Gelatin capsules

The capsule filler composition is compounded from the following ingredients:

| | |
|---|---|
| 2-Methyl-2-{4-[2-(2-methoxy-5-chloro-benzamido)-ethyl]-biphenyl-4'-oxy}-propionic acid | 5.0 parts |
| Corn starch dried | 100.0 parts |
| Corn starch powdered | 93.0 parts |
| Magnesium stearate | 2.0 parts |
| Total | 200.0 parts |

Preparation

The ingredients are admixed with each other, the mixture is passed through a 0.75 mm mesh screen, and the screened composition is homogenized in a suitable mixer. 200 mgm portions of the resulting powder are filled into No. 3 hard gelatin capsules. Each capsule contains 5 mgm of the active ingredient and is an oral dosage unit composition with effective antihyperlipidemic action

EXAMPLE 15

Tablets

The tablet composition is compounded from the following ingredients:

| | |
|---|---|
| 2-Methyl-2-{4-[2-(2-methoxy-5-chloro-benzamido)-ethyl]-biphenyl-4'-oxy}-propionic acid | 25.0 parts |
| Lactose | 35.0 parts |
| Corn starch | 15.0 parts |
| polyvinylpyrrolidone | 4.5 parts |
| Magnesium stearate | 0.5 parts |
| Total | 80.0 parts |

Preparation

The active ingredient, the lactose and the corn starch are intimately admixed with each other; the mixture is uniformly moistened with an aqueous solution of the polyvinylpyrrolidone, the moist mass is forced through a 1.5 mm mesh screen, and the resulting granulate is dried at 45° C in a drying chamber with circulating air and again passed through a 1.0 mm mesh screen. The dry granulate is admixed with the magnesium stearate, and the composition is compressed into 80 mgm tablets in a conventional tablet making machine. Each tablet contains 25 mgm of the active ingredient and is an oral dosage unit composition with effective antihyperlipidemic action.

EXAMPLE 16

Coated pills

The pill core composition is compounded from the same ingredients and in the same manner as the tablet composition of the preceding example, and the composition is compressed into 80 mgm pill cores. The cores are then coated with a thin shell consisting essentially of a mixture of talcum and sugar, and the coated pills are finally polished with beeswax. Each coated pill contains 25 mgm of the active ingredient and is an oral dosage unit composition with effective antihyperlipidemic action.

Analogous results are obtained when any one of the other compounds embraced by formula I or a non-toxic salt thereof is substituted for the particular active ingredient in Examples 13 through 16. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

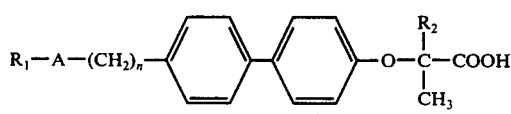

wherein $R_1$ is alkyl of 1 to 6 carbon atoms, cycloalkyl of 3 to 6 carbon atoms, phenylalkyl, phenylalkenyl or

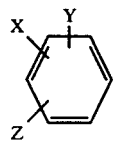

where

X, Y and Z are each hydrogen, halogen, alkyl of 1 to 3 carbon atoms or alkoxy of 1 to 3 carbon atoms, $R_2$ is hydrogen or alkyl of 1 to 4 carbon atoms, A is —CO—NH— or —NH—CO—, and $n$ is 1, 2 or 3, or a non-toxic salt thereof formed with an inorganic or organic base.

2. A compound of claim 1 of the formula

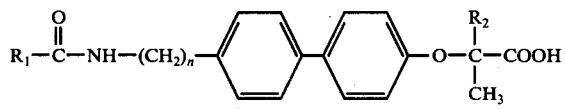

wherein $R_1$ is alkyl of 1 to 6 carbon atoms, cycloalkyl of 3 to 6 carbon atoms, phenylalkyl, phenylalkenyl or

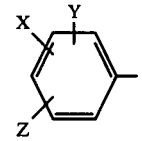

where

X, Y and Z are each hydrogen, halogen, alkyl of 1 to 3 carbon atoms of alkoxy of 1 to 3 carbon atoms, $R_2$ is hydrogen or alkyl of 1 to 4 carbon atoms, and $n$ is 1, 2 or 3, or a non-toxic salt thereof formed with an inorganic or organic base.

3. A compound of claim 2 of the formula

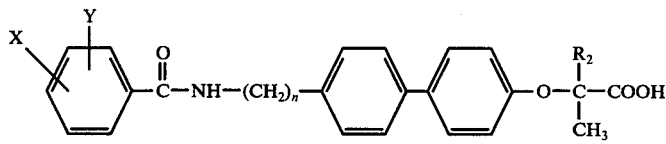

wherein $R_2$ is hydrogen or methyl,

X and Y are each hydrogen, fluorine, chlorine, bromine, methyl or methoxy, and $n$ is 1, 2 or 3, or a non-toxic salt thereof formed with an inorganic or organic base.

4. A compound of claim 3, which is 2-methyl-2-{4-[2-(2-methoxy-5-chloro-benzamido)-ethyl]-biphenyl-4'-oxy}-propionic acid or a non-toxic salt thereof formed with an inorganic or organic base.

5. A compound of claim 3, which is 2-methyl-2-{4-[2-(2-methoxy-benzamido)-ethyl]-biphenyl-4'-oxy}-propionic acid or a non-toxic salt thereof formed with an inorganic or organic base.

6. An antihyperlipidemic pharmaceutical dosage unit composition consisting essentially of an inert pharmaceutical carrier and an effective antihyperlipidemic amount of a compound of claim 1.

7. The method of lowering the level of lipids in the blood of a warm-blooded animal in need of such treatment, which comprises perorally, parenterally or rectally administering to said animal an effective antihyperlipidemic amount of a compound of claim 1.

* * * * *